United States Patent
Sato et al.

(10) Patent No.: US 9,766,316 B2
(45) Date of Patent: Sep. 19, 2017

(54) MAGNETIC RESONANCE IMAGING DEVICE AND QUANTITATIVE SUSCEPTIBILITY MAPPING METHOD

(71) Applicant: Hitachi, Ltd., Tokyo (JP)

(72) Inventors: Ryota Sato, Tokyo (JP); Toru Shirai, Tokyo (JP); Yo Taniguchi, Tokyo (JP); Yoshihisa Soutome, Tokyo (JP); Yoshitaka Bito, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 137 days.

(21) Appl. No.: 14/442,168

(22) PCT Filed: Nov. 16, 2012

(86) PCT No.: PCT/JP2012/079728
§ 371 (c)(1),
(2) Date: May 12, 2015

(87) PCT Pub. No.: WO2014/076808
PCT Pub. Date: May 22, 2014

(65) Prior Publication Data
US 2015/0338492 A1    Nov. 26, 2015

(51) Int. Cl.
*G01R 33/565*    (2006.01)
*G01R 33/48*    (2006.01)
(Continued)

(52) U.S. Cl.
CPC ........ *G01R 33/56536* (2013.01); *A61B 5/055* (2013.01); *G01R 33/4818* (2013.01);
(Continued)

(58) Field of Classification Search
CPC .... G01R 33/56536; G01R 33/00; A61B 5/00; A61B 2576/00
See application file for complete search history.

(56) References Cited

U.S. PATENT DOCUMENTS 6,658,280 B1* 12/2003 Haacke .............. A61B 5/02007
324/306
7,573,265 B2* 8/2009 Haacke ................ G01R 33/565
324/306
(Continued)

FOREIGN PATENT DOCUMENTS

WO    2009/081787 A1    7/2009
WO    2010/073923 A1    7/2010

OTHER PUBLICATIONS

Liu, Jing, et al. "Morphology enabled dipole inversion for quantitative susceptibility mapping using structural consistency between the magnitude image and the susceptibility map." Neuroimage 59.3 (2012): 2560-2568.*
(Continued)

*Primary Examiner* — Long V Le
*Assistant Examiner* — Sean D Mattson
(74) *Attorney, Agent, or Firm* — Mattingly & Malur, PC

(57) ABSTRACT

The estimation accuracy of a magnetic susceptibility value of tissue is improved by computing an edge image which represents the edge of the tissue on a magnetic susceptibility distribution and to reduce background noise without lowering the magnetic susceptibility value of the tissue. The present invention computes an absolute value image and a phase image from a complex image obtained by MRI, from the phase image, computes a low frequency region magnetic susceptibility image in which background noise is greater than a desired value, computes an edge information magnetic susceptibility image and computes a high frequency region magnetic susceptibility image, computes an edge mask from the edge information magnetic susceptibility image, smooths a magic angle region from the edge mask and the low frequency region magnetic susceptibility image
(Continued)

and finally smooths a high frequency region using the high frequency region magnetic susceptibility image.

9 Claims, 9 Drawing Sheets

(51) Int. Cl.
    *G01R 33/50*     (2006.01)
    *A61B 5/055*     (2006.01)
    *G01R 33/56*     (2006.01)
    *G01R 33/561*     (2006.01)

(52) U.S. Cl.
    CPC ......... *G01R 33/4828* (2013.01); *G01R 33/50* (2013.01); *G01R 33/5608* (2013.01); *A61B 2576/00* (2013.01); *G01R 33/5613* (2013.01)

(56) References Cited

U.S. PATENT DOCUMENTS

| | | |
|---|---|---|
| 8,422,756 B2 | 4/2013 | Haacke et al. |
| 8,781,197 B2 | 7/2014 | Wang et al. |
| 2008/0071167 A1* | 3/2008 | Ikedo ............... G01R 33/56545 600/419 |
| 2009/0261824 A1* | 10/2009 | Haacke ............ G01R 33/56536 324/307 |
| 2011/0044524 A1* | 2/2011 | Wang ..................... G01R 33/54 382/131 |
| 2011/0262017 A1* | 10/2011 | Haacke ................ G01R 33/443 382/131 |

OTHER PUBLICATIONS

Schweser, Ferdinand, et al. "Quantitative susceptibility mapping for investigating subtle susceptibility variations in the human brain." Neuroimage 62.3 (2012): 2083-2100.*
Tian Liu et al., Morphology Enabled Dipole Inversion (MEDI) from a Single-Angle Acquisition: Comparison with Cosmos in Human Brain Imaging, Magnetic Resonance in Medicine, 2011, pp. 777-783, vol. 66, No. 3.
F. Schweser et al., Quantitative susceptibility mapping for investigating subtle susceptibility variations in the human brain, Neuro Image, 2012, pp. 2083-2100, vol. 62, No. 3.

* cited by examiner

MAGNETIC RESONANCE IMAGING DEVICE AND QUANTITATIVE SUSCEPTIBILITY MAPPING METHOD

TECHNICAL FIELD

The invention relates to a magnetic resonance imaging (MRI) technique. Particularly, it relates to a technique for image processing of reconstructed images.

BACKGROUND ART

A magnetic resonance imaging device (hereinafter, referred to as MRI device) is a diagnostic imaging apparatus for medical use, which applies a high frequency magnetic field and a gradient magnetic field to a subject placed in a static magnetic field, measures signals generated from the subject by nuclear magnetic resonance, and forms an image from the signals.

In the MRI device, generally, a slice gradient magnetic field for specifying an imaging cross section and an excitation pulse (high frequency magnetic filed pulse) for exciting magnetization in the cross section are simultaneously applied, hence to obtain nuclear magnetic resonance signals (echoes) generated during the process of converging the excited magnetization. Here, in order to impart three-dimensional positional information to the magnetization, a phase encoding gradient magnetic field and a readout gradient magnetic field vertical to each other are applied to a slice gradient magnetic field and an imaging cross section, during the period from excitation to acquisition of echoes. The measured echoes are arranged in a k space with axes kx, ky, and kz, and subjected to the inverse Fourier transform to perform image reconstruction.

Each of the pixel values of the reconstructed image becomes a complex number including an absolute value and a declination (phase). A gray scale image (absolute value image) having pixel values of absolute values is an image in which density of protons (hydrogen nuclei) and relaxation time (T1, T2) are reflected, excellent in visualizing a tissue structure. On the other hand, a gray scale image (phase image) having pixel values of phase is an image which reflects a magnetic field change caused by non-uniformity of static magnetic field and difference of magnetic susceptibility between living tissues.

Recently, there has been proposed a quantitative susceptibility mapping (Quantitatively Susceptibility Mapping: QSM) method in which based on the fact that the phase images reflect difference of magnetic susceptibility between tissues, a magnetic susceptibility distribution inside a living body is estimated from the phase images. It is known that the magnetic susceptibility of the living body tissue varies depending on the amount of iron and the amount of oxygen inside vein. A variation of the magnetic susceptibility provides useful information for diagnosis of neurodegenerative diseases and stroke.

For example, in the patients of Alzheimer's disease, one of the neurodegenerative diseases, it is known that according to the progress of the disease, iron deposition in plural tissues in a brain such as a tissue called putamen is increased, resulting in increasing the magnetic susceptibility. Therefore, if magnetic susceptibility of these tissues can be measured, it is expected that the objective information about the degree of the progress in the Alzheimer's disease can be obtained. Here, a magnetic susceptibility of a tissue is defined by the average magnetic susceptibility value in ROI (Region of Interest) set at arbitrary size within a target tissue.

In order to estimate a magnetic susceptibility distribution in a brain, a relational expression of a phase distribution $\phi$ and a magnetic susceptibility distribution $\chi$ expressed by the following formula (1) is used.

$$\phi(r) = -\frac{\gamma B_0 \tau_{TE}}{4\pi} \int \chi(r') \frac{3\cos^2\alpha - 1}{|r'-r|^3} d^3 r' \quad \text{(formula 1)}$$

In the formula (1), $\phi(r)$ represents phase (rad) at a position r, $\gamma$ represents magnetic rotation ratio of protons, $B_0$ represents static magnetic field strength (T), $\tau_{TE}$ represents TE (Echo Time) (s), $\chi(r')$ represents magnetic susceptibility (ppm) at the position r', $\alpha$ is an angle made by a static magnetic field direction and a vector r'–r. However, in order to estimate a magnetic susceptibility distribution from the phase image using the formula (1), convolution integral of a right side has to be inversely solved. This is an inverse problem and a solution is not uniquely determined; therefore, an accurate magnetic susceptibility distribution cannot be uniquely estimated.

Accordingly, QSM method is used to estimate an approximate magnetic susceptibility distribution and form the image. Hereinafter, the magnetic susceptibility distribution approximately estimated based on the formula (1) and imaged is called a magnetic susceptibility image. The magnetic susceptibility image varies according to a calculation method and parameters used for calculation.

In these days, various QSM methods are proposed in order to calculate a magnetic susceptibility of tissue with high accuracy. For the above purpose, it is necessary to require a signal in a region in the vicinity of magic angle on the k space of the magnetic susceptibility image as accurate as possible. A relational expression of the phase distribution and the magnetic susceptibility distribution on the k space is expressed by the formula (2) which results from the Fourier transform of the formula (1), with the static magnetic field direction defined as a z direction.

$$\Delta(k) = \left(\frac{1}{3} - \frac{k_z^2}{k^2}\right) \cdot X(k) \quad \text{(formula 2)}$$

Where, k represents position vector on the k space, $k_z$ represents z component of the vector k, $\Delta$ represents phase distribution on the k space, and X represents magnetic susceptibility distribution on the k space.

Here, the magic angle indicates the angle of 55 degree or 135 degree with respect to the static magnetic field direction from the origin center of the k space, corresponding to the region of $(1/3 - k_z^2/k^2) = 0$ in the formula (2).

Hereinafter, a region in the vicinity of the magic angle on the k space is defined as a magic angle region. The magic angle region is defined by a region satisfying the expression of $|1/3 - k_z^2/k^2| < a_{th}$ using some threshold $a_{th}$. The threshold $a_{th}$ is defined as a magic angle threshold. It is known that in the magic angle region of the magnetic susceptibility image, noise is most increased and that magnetic susceptibility information of tissue is buried in the noise and lost. On the other hand, in a region other than the magic angle region, noise exists but the magnetic susceptibility information of tissue is not lost. Therefore, if the magnetic susceptibility information of tissue in the magic angle region of the k space can be calculated with high accuracy, magnetic susceptibility of tissue can be calculated with high accuracy.

In order to solve the above problems, recently, as a useful method, there has been proposed a method of calculating an edge image indicating the edge region of a tissue in advance and smoothing the region other than the edge in the magnetic susceptibility image by using the above image. The edge image means an image having larger pixel values in the edge region of a tissue than the pixel values in the other region. If the edge image indicating the edge region of a tissue on the magnetic susceptibility distribution can be calculated in advance, the magnetic susceptibility value corresponding to the magic angle region is smoothed by using the above, hence to reduce the background noise, which can improve the estimation accuracy in the magnetic susceptibility of tissue. Here, the background noise is defined by a standard deviation for ROI, for example, set in some region of a brain parenchyma on the magnetic susceptibility image. Of the methods using the edge image of these days, the typical ones are MEDI (Morphology enabled dipole inversion) method (Non-Patent Document 1) and HEIDI (Homogeneity Enabled Incremental Dipole Inversion) method (Non-Patent Document 2).

CITATION LIST

Non-Patent Documents

Non-Patent Document 1: Morphology enabled dipole inversion (MEDI) from a single-angle acquisition: comparison with COSMOS in human brain imaging, Magnetic Resonance in Medicine, p. 777-783, volume 66, No. 3, (2011), written by Liu T et al.
Non-Patent Document 2: Quantitative susceptibility mapping for investigating subtle susceptibility variations in the human brain, Neuro Image, p. 2083-2100, volume 62, No. 3, (2012), written by Schweser F et al.

SUMMARY OF INVENTION

Technical Problem

The MEDI method is a method of creating an edge image from an absolute value image, on the assumption that a tissue represented in the absolute value image is similar to the edge of the tissue represented in the magnetic susceptibility distribution, smoothing the region other than the edge, and calculating a magnetic susceptibility image. According to the MEDI method, the magnetic susceptibility image with less background noise can be obtained.

However, in a region where the absolute value image does not agree with the edge of the magnetic susceptibility distribution, there is a problem that the estimation accuracy in the magnetic susceptibility is deteriorated. Further, the magnetic susceptibility value corresponding to the region other than the magic angle region is also smoothed, and as the result, the magnetic susceptibility value of tissue is decreased according to the effect of the smoothing, hence to deteriorate the estimation accuracy.

The HEIDI method is a method of creating an edge image of a tissue from a phase image, on the assumption that a tissue represented in the phase image is similar to the edge of the tissue represented in the magnetic susceptibility distribution, adding Laplace filtered image of the phase image and the edge information obtained from the absolute value image to the above edge image, smoothing the region other than the edge, and calculating a magnetic susceptibility image. As illustrated in FIG. 10, smoothing is performed only on the magnetic susceptibility values corresponding to a magic angle region 902 and its peripheral region 903 on the k space of the magnetic susceptibility image.

The phase image, however, varies in the contrast of the image according to the magnetic field direction, and the edge image of tissue extracted from the phase image varies according to the magnetic field direction, which deteriorates the estimation accuracy in the magnetic susceptibility of tissue. Further, the edge image has to be calculated from three images, and therefore, the number of parameters necessary for calculation of the edge image is increased, which makes the processing complicated. When the magnetic susceptibility value corresponding to the peripheral region 903 of the magic angle is smoothed, the magnetic susceptibility information of tissue exists in a low frequency region, and therefore, the magnetic susceptibility value of tissue is reduced according to the effect of the smoothing, similarly to the MEDI method, hence to deteriorate the estimation accuracy.

Taking the above situation into consideration, the invention is to provide a technique for improving the estimation accuracy in the magnetic susceptibility of tissue by calculating a correct edge image representing the tissue on the magnetic susceptibility distribution, and reducing the background noise without reducing the magnetic susceptibility value of the tissue.

Solution to Problem

As one example for resolving the above problems, there is provided a magnetic resonance imaging device comprising a static magnetic field applying part for applying a static magnetic field to a subject, a gradient magnetic field applying part for applying a gradient magnetic field to the subject, a high frequency magnetic field pulse irradiating part for irradiating the subject with a high frequency magnetic field pulse, a receiving part for receiving a nuclear magnetic resonance signal from the subject, and a computing part for calculating the nuclear magnetic resonance signal received by controlling the gradient magnetic field and the high frequency magnetic field pulse, wherein the computing part includes a measurement unit for detecting the nuclear magnetic resonance signal generated from the subject as a complex signal by applying the high frequency magnetic field pulse and the gradient magnetic field to the subject placed in the static magnetic field, an image reconstruction unit for reconstructing a complex image in which each pixel value is a complex image, from the complex signal, an image conversion unit for converting the complex image into a magnetic susceptibility image, and a display processing unit for displaying the created image on a display; the image conversion unit includes a complex image conversion unit for creating an absolute value image and a phase image from the complex image, and a magnetic susceptibility image calculation unit for creating the magnetic susceptibility image from the phase image; and the magnetic susceptibility image calculation unit includes an edge information magnetic susceptibility image calculation unit for calculating an edge information magnetic susceptibility image indicating an edge of a tissue in a magnetic susceptibility distribution, and an edge mask calculation unit for calculating an edge mask of a tissue from the edge information magnetic susceptibility image.

Advantageous Effects of Invention

The magnetic susceptibility of tissue can be calculated with high accuracy by calculating the edge image of a tissue on the magnetic susceptibility distribution and smoothing the magnetic susceptibility image using the edge image.

DESCRIPTION OF EMBODIMENTS

Figure 1:
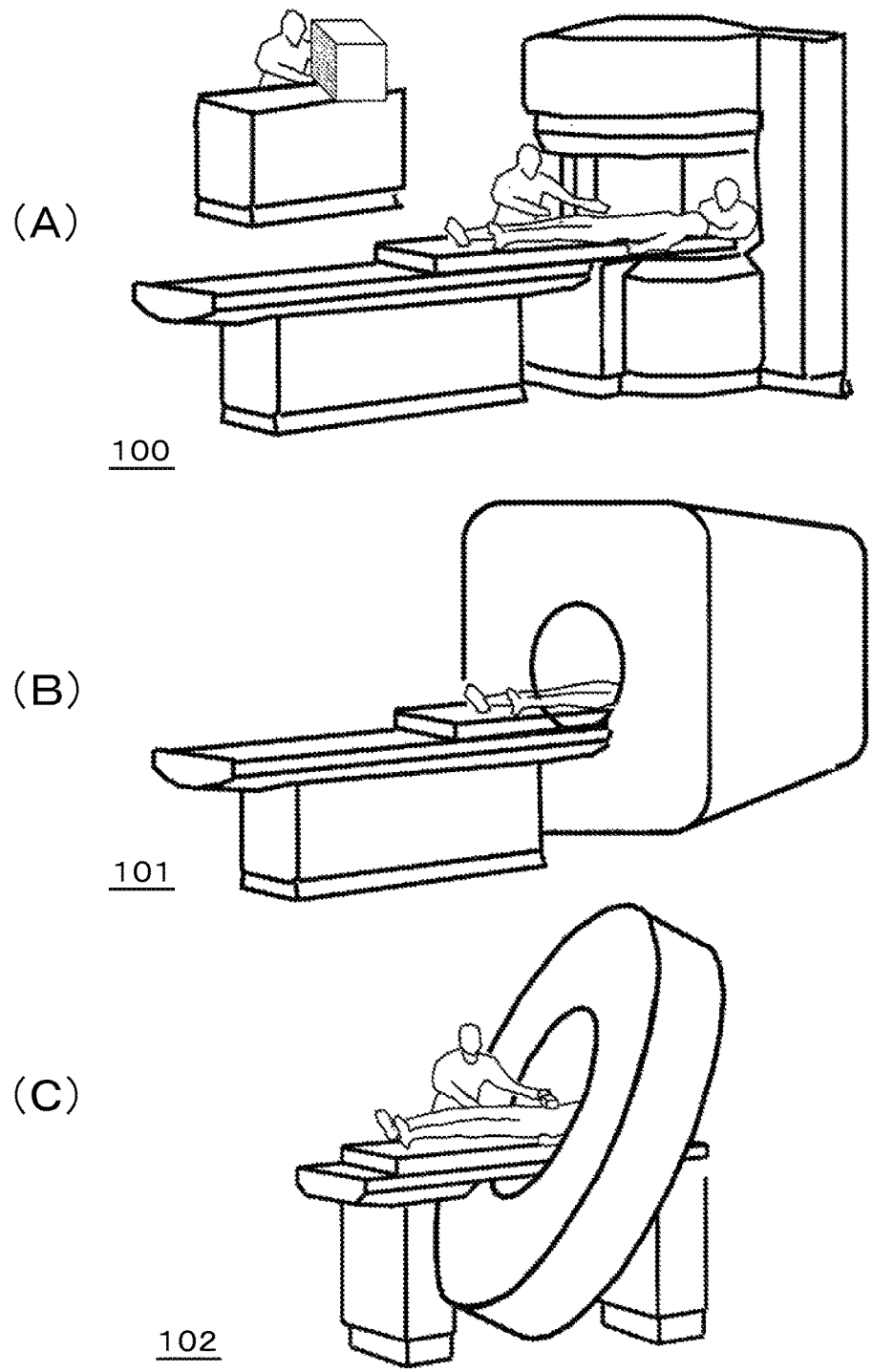
FIG. 1(a) is an appearance view of a magnetic resonance imaging device of vertical magnetic field type, FIG. 1 (b) is an appearance view of a magnetic resonance imaging device of horizontal magnetic field type.
FIG. 1(c) is an appearance view of a magnetic resonance imaging device in which a sense of freedom is improved.

Hereinafter, embodiments of the invention will be described with reference to the drawings. In all the drawings for use in describing the embodiments of the invention, components having the same functions are indicated with the same reference numerals and the repetitive description thereof is omitted. The invention is not to be restricted by the following description.

First Embodiment

A first embodiment of the invention will be described. At first, an MRI device of the embodiment will be described. FIGS. 1(a) to 1(c) are appearance views of the MRI device according to the embodiment. FIG. 1(a) is an MRI device 100 of a vertical magnetic field type (vertical magnetic field MRI) in a hamburger shape (open type) with magnet vertically separated to improve the sense of freedom. FIG. 1(b) is an MRI device 101 of a horizontal magnetic field type (horizontal magnetic field MRI) using a tunnel-shaped magnet which generates a static magnetic field with a solenoid coil. FIG. 1(c) is an MRI device 102, using the tunnel-shaped magnet, similar to FIG. 1(b), which is formed in a shorter depth of the magnet being inclined, to further improve the sense of freedom. The forms of the MRI device are only one example of each of the vertical magnetic field type and the horizontal magnetic field type and the MRI device is not restricted to the above.

Hereinafter, the embodiment will be described, by way of example, taking the case of using the horizontal magnetic field type MRI device 101 illustrated in FIG. 1(b). Hereinafter, the embodiment uses a coordinate system with a static magnetic field direction of the MRI device 101 defined as a z direction, and of the two directions vertical to the z direction, a direction parallel to a bed surface to put a target subject to be measured defined as an x direction and the other direction defined as a y direction. Hereinafter, the static magnetic field is simply referred to a magnetic field.

Figure 2:
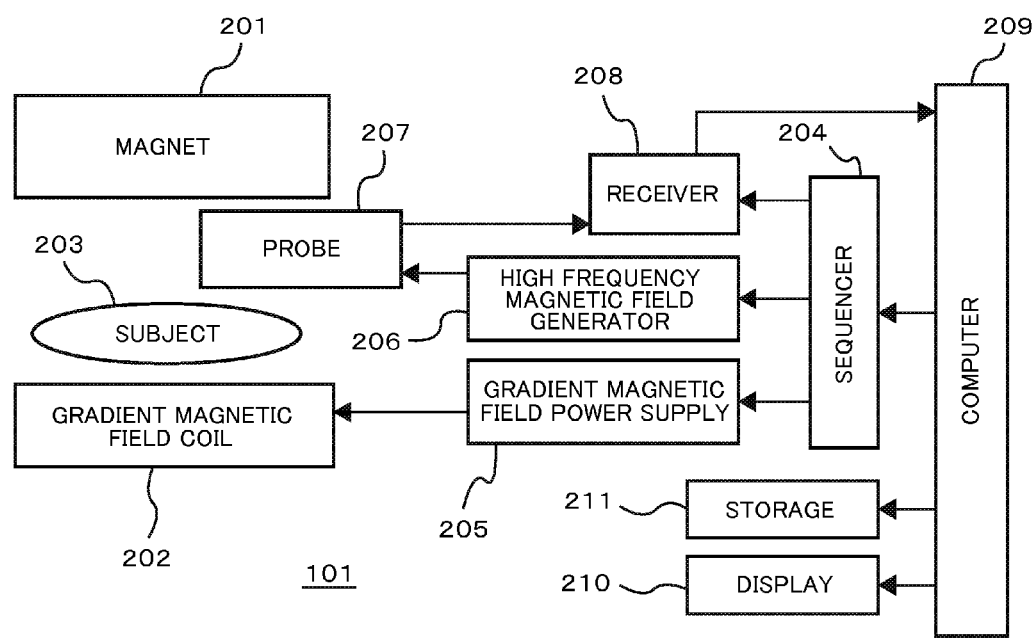
FIG. 2 is a block diagram showing a schematic structure of an MRI device in the embodiment.
Figure 3:
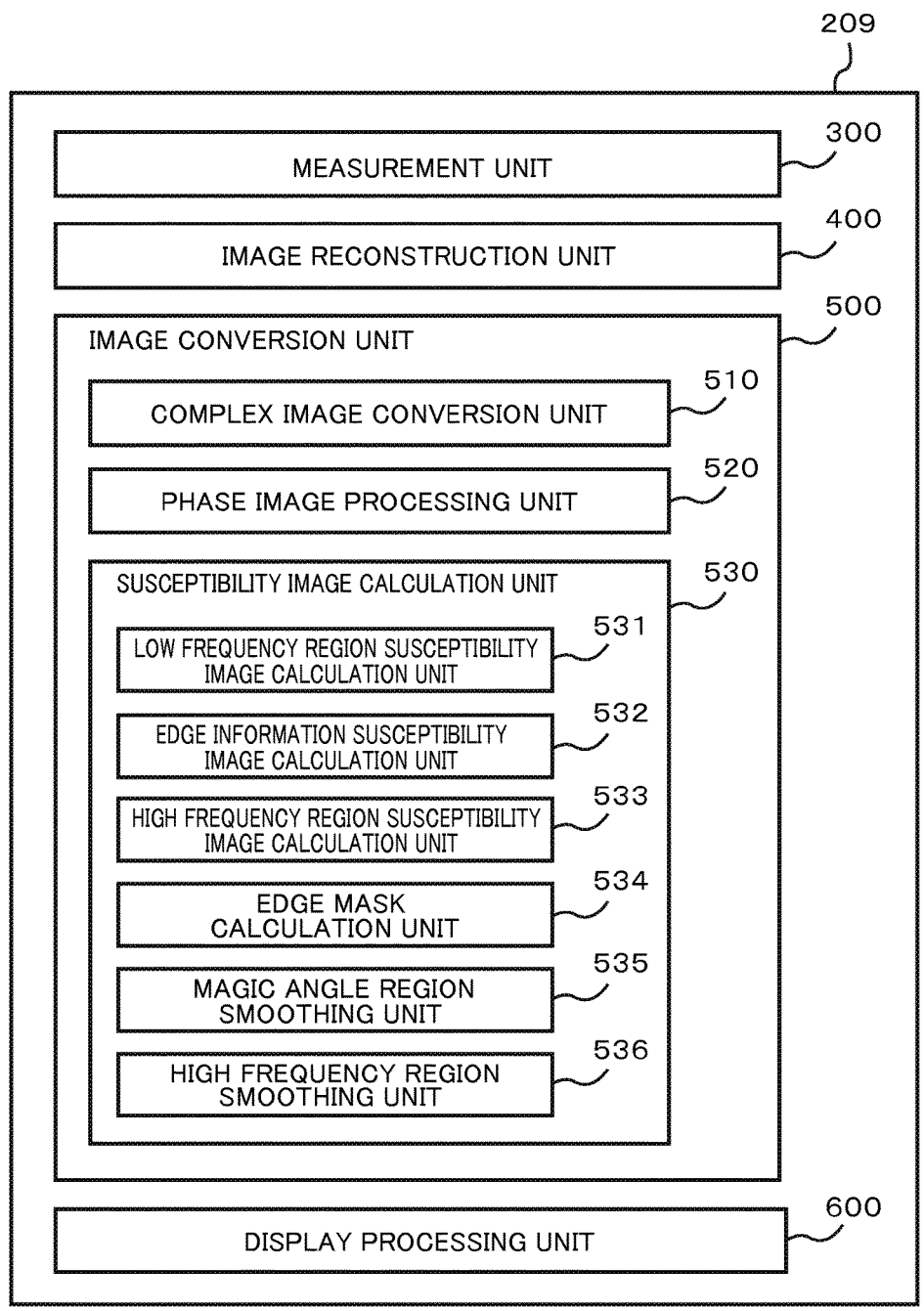
FIG. 3 is a functional block diagram of a computer in the embodiment.

FIG. 2 is a block diagram illustrating the schematic structure of the MRI device 101 according to the embodiment. The MRI device 101 includes a magnet 201 for generating a static magnetic field in a parallel to the subject, a gradient magnetic field coil 202 for generating a gradient magnetic field, a sequencer 204, a gradient magnetic field power supply 205, a high frequency magnetic field generator 206, a probe 207 for irradiating a high frequency magnetic field and detecting nuclear magnetic resonance signals (echoes), a receiver 208, a computer 209, a display 210, and a storage 211. A subject (for example, a living body) 203 is put on a bed (table) and arranged in a static magnetic field space generated by the magnet 201. In the embodiment, an imaging target is supposed to be a brain.

Therefore, a head of the subject is arranged in the static magnetic field space. Needless to say, the imaging target is not restricted to a brain but may be any organ such as liver or heart.

The sequencer 204 sends an instruction to the gradient magnetic field power supply 205 and the high frequency magnetic field generator 206, to generate a gradient magnetic field and a high frequency magnetic field respectively. The generated high frequency magnetic field is applied to the subject 203 through the probe 207. The echoes generated from the subject 203 are received by the probe 207 and detected by the receiver 208.

Nuclear magnetic resonance frequency (detection reference frequency f0) as a reference of detection is set by the sequencer 204. The detected signals are sent to the computer 209, where signal processing such as image reconstruction is performed. The result is displayed on the display 210. Depending on necessity, the detected signals, measurement conditions, and the image information obtained after the signal processing may be stored in the storage 211. The sequencer 204 controls each unit to operate at each timing and strength previously programmed. Of the programs, especially a program describing each timing and strength of a high frequency magnetic field, a gradient magnetic field, and signal receiving is called a pulse sequence.

Various pulse sequences depending on the purpose are known and any pulse sequence can be used here. The MRI device 101 of the embodiment uses a pulse sequence of GrE (Gradient Echo) system capable of obtaining signals depending on the non-uniformity in a spatial distribution of magnetic field strength. The pulse sequence of the GrE system includes, for example, an RSSG (RF-spoiled-Steady-state Acquisition with Rewound Gradient-Echo) sequence.

The computer 209 of the embodiment instructs the sequencer 204 to measure echoes according to the set measurement parameters and pulse sequence, disposes the obtained echoes in the k space, calculates the echoes disposed in the k space, creates its image of a desired contrast, and displays the obtained image on the display 210.

The respective functions of the computer 209 are realized by the CPU of the computer 209 loading programs stored in the storage 211 into a memory and executing the programs.

Figure 4:
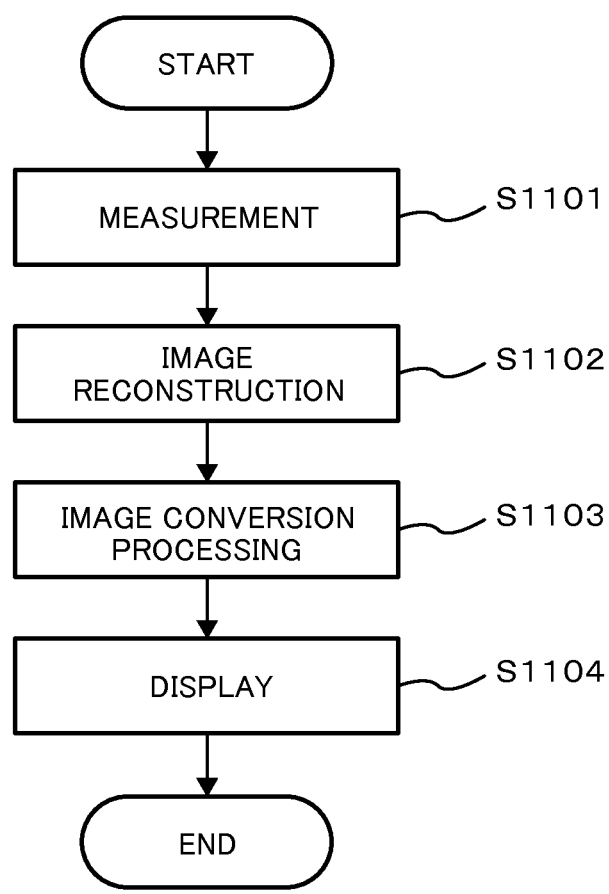
FIG. 4 is a flow chart of imaging processing in the embodiment.

Hereinafter, the detailed imaging processing by a measurement unit 300, an image reconstruction unit 400, an image conversion unit 500, a display processing unit 600 of the computer 209 according to the embodiment will be described according to the flow of the processing. FIG. 4 is the processing flow of the imaging processing in the embodiment.

When various measurement parameters are set, upon receipt of the instruction to start the imaging, the measurement unit 300 performs the measurement (Step S1101). Here, according to the predetermined pulse sequence, the measurement unit 300 instructs the sequencer 204 to obtain echo signals and dispose the signals in the k space. The sequencer 204 sends the command to the gradient magnetic field power supply 205 and the high frequency magnetic field generator 206, according to the instruction, as mentioned above, to generate a gradient magnetic field and a high frequency magnetic field respectively. The sequencer 204 receives the echoes received by the probe 207 and detected by the receiver 208, as complex signals.

In the embodiment, as mentioned above, the pulse sequence of GrE system is used. The pulse sequence of GrE system used in the embodiment will be described by using the RSSG sequence as an example.

Figure 5:
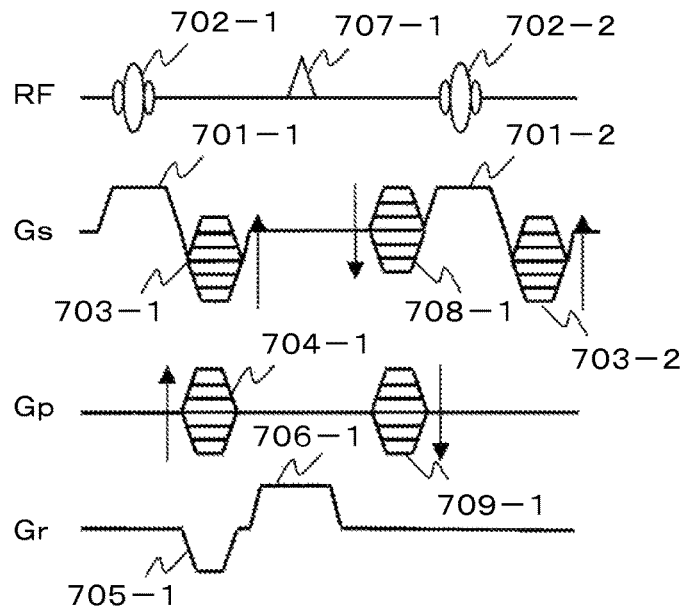
FIG. 5 is a pulse sequence view of RSSG (RF-spoiled-Steady-state Acquisition with Rewound Gradient-Echo) sequence.

FIG. 5 is a pulse sequence view of the RSSG sequence. In FIG. 5, RF, Gs, Gp, and Gr respectively indicate a high frequency magnetic field, a slice gradient magnetic field, a phase encoding gradient magnetic field, and a readout gradient magnetic field.

In the RSSG sequence, a slice gradient magnetic field pulse 701 and a high frequency magnetic field (RF) pulse 702 are simultaneously applied to excite the magnetization in a predetermined slice of the subject 203. Then, a slice encoding gradient magnetic field pulse 703 and a phase encoding gradient magnetic field pulse 704 are applied for imparting the positional information in a slice direction and a phase encoding respectively to the phase of the magnetization.

After applying a readout gradient magnetic field pulse for dephasing 705 which disperses the phase of the nuclear magnetization in the pixels, one nuclear magnetic resonance signal (echo) 707 is measured while applying a readout gradient magnetic field pulse 706 for imparting the positional information in the read out direction. Then, a slice encoding gradient magnetic field pulse 708 and a phase encoding gradient magnetic field pulse 709 for rephasing are applied to converge the phase of the nuclear magnetization dephased by the slice encoding gradient magnetic field pulse 703 and the phase encoding gradient magnetic field pulse 704.

The measurement unit 300 executes the above procedure at a cycle of a repetition time TR, while changing the strength of the slice encoding gradient magnetic field pulses 703 and 708 (slice encoding number ks) and the phase encoding gradient magnetic field pulses 704 and 709 (phase encoding number kp) and the phase of the RF pulse 702, to measure the echoes necessary for obtaining one image. At this time, the phase of the RF pulse 702 is increased by, for example, every 117 degree. In FIG. 5, the number after hyphen indicates the number of repetition.

The measured echoes are disposed in a three dimensional k space with the coordinate axes kr, kp, and ks. At this point, one echo occupies one line in parallel to the kr axis in the k space. When TE (time from the irradiation of the RF pulse 702 to the measurement of the echo 707) is set short, the absolute value image obtained according to the RSSG sequence becomes T1 (longitudinal relaxing time) weighted image and when the TE is set long, the absolute value image becomes T2* weighted image reflecting the phase dispersion in the pixels.

In the embodiment, the RSSG sequence that is one of the Cartesian imaging for obtaining data in parallel to the coordinate axes of the k space is used; however, any sequence can be used to obtain the data in some k space region.

For example, one TR may obtain a plurality of echoes and the echoes may be disposed in various k space images. Alternatively, one complex image or phase image may be created from the separate complex images or phase images obtained from a plurality of echoes. Further, non-Cartesian imaging may be used such as a radial scan for obtaining data in a rotation pattern in a k space.

Alternatively, imaging is performed several times, to obtain respective data in separate k space regions and the integrated data may be used.

After the measurement, the image reconstruction unit 400 performs image reconstruction processing for reconstructing the image according to the echo signals disposed in the k space (Step S1102). Here, the image reconstruction unit 400 performs processing such as the three dimensional inverse Fourier transform on the echoes (data) disposed in the k space and reconstructs a complex image in which each pixel value is represented by a complex number.

The image conversion unit 500 performs various image conversion processing described later on the obtained complex image (Step S1103). In the embodiment, the image conversion unit 500 converts the complex image obtained by the image reconstruction unit 400 into a magnetic susceptibility image. The details of the image conversion processing in the embodiment will be described later.

The display processing unit 600 in the embodiment displays the obtained magnetic susceptibility image on the display 210 as a gray scale image (Step S1104). A plurality of image information may be integrated and displayed using a method such as the maximum projection processing. Further, the image processing is performed on the magnetic susceptibility image, to create an image of different contrast from the magnetic susceptibility image and the same image may be displayed on the display 210. For example, a weighted mask with a magnetic susceptibility difference between tissues weighted from the magnetic susceptibility image may be created and a magnetic susceptibility difference weighted image obtained by multiplying the weighted mask by the absolute value image may be displayed. The magnetic susceptibility difference weighted image loses the magnetic susceptibility information of the tissues because of the processing of weighting the magnetic susceptibility difference; however, contrast between a tissue having a high magnetic susceptibility and the other tissue is increased. Therefore, the tissues having a high magnetic susceptibility are clearly extracted.

Figure 6:
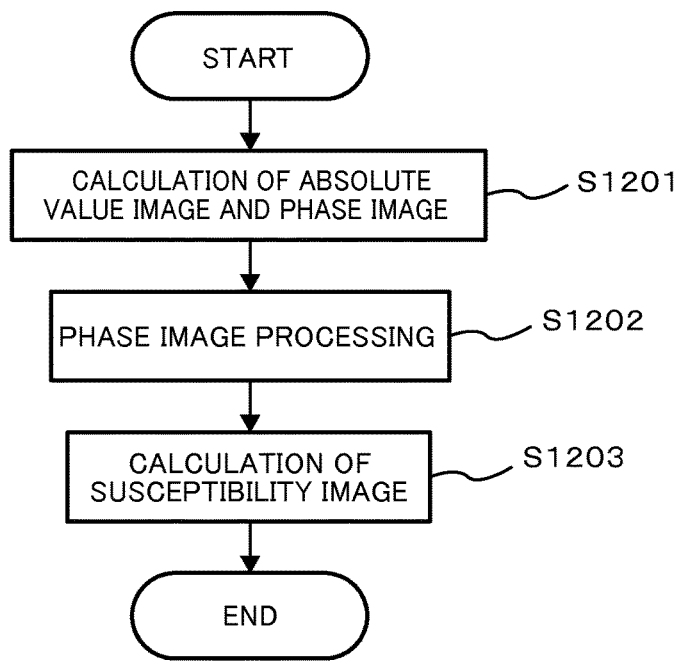
FIG. 6 is a flow chart of image conversion processing in the embodiment.

Hereinafter, the flow of the image conversion processing will be described in the embodiment. FIG. 6 is a processing flow of the image conversion processing according to the embodiment.

When the image conversion processing is started, the image conversion unit 500 in the embodiment generates an absolute value image and a phase image from the complex image generated by the image reconstruction unit 510 (Step S1201). The absolute value image and the phase image are respectively created from the absolute value components and the phase components as for the complex numbers of the pixels of the complex image. The pixel value $S(i)$ of the absolute value image and the pixel value $\phi(i)$ of the phase image in the pixel i are calculated using the pixel value $c(i)$ of the complex image, respectively according to the formula (3) and the formula(4).

$$S(i)=|c(i)| \qquad \text{(formula 3)}$$

$$\phi(i)=\arg\{c(i)\} \quad \text{(formula 4)}$$

Figure 7:
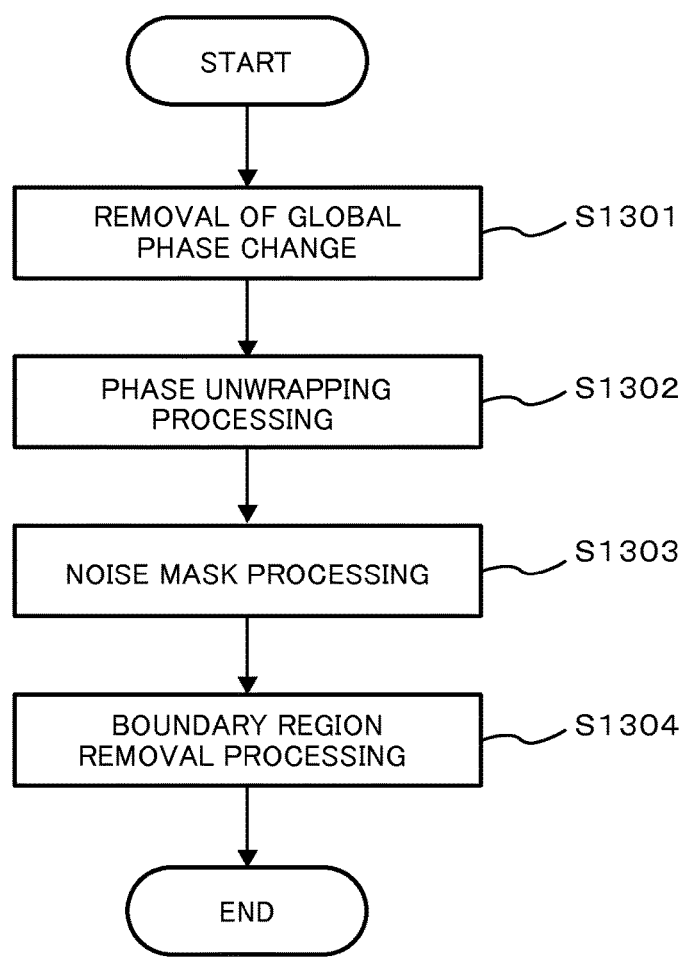
FIG. 7 is a flow chart of phase image processing in the embodiment.

Next, the phase image processing described later is performed on the phase image (Step S1202). In the embodiment, four types of the phase image processing are performed. The four types of the phase image processing are hereinafter described with reference to the processing flow of FIG. 7.

At first, global phase change removal processing for removing a global phase change from the phase image is performed (Step S1301). The phase image calculated by the formula (4) is the sum of the global phase change caused by the non-uniformity of the static magnetic field generated depending on the shape of a target imaging portion (for example, head etc.) and a local phase change caused by the magnetic susceptibility change between tissues.

Further, the global change and the local change respectively correspond to the low frequency components and the high frequency components in the k space of the phase image. According to this processing, only the global phase change can be removed and therefore, the local phase change caused by the magnetic susceptibility change between tissues can be calculated. According to the global phase change removal processing in the embodiment, low pass filter processing is first performed for every two-dimensional image for the obtained three-dimensional image (original image) to calculate a low resolution image.

Then, the global phase change contained in the low resolution image is removed from the original image by complex division of the original image with the low resolution image. There are various methods as the method for removing a global phase change. For example, there is a method of extracting a global phase change by fitting of a three-dimensional image with a low order polynomial and subtracting the above from an original image. For the global phase change removal processing, another method like this may also be used.

Then, phase unwrapping processing for correcting the wrapped phase is performed (Step S1302). In a partial region of the phase image, phase values out of the range of $-\pi$ to $\pi$ are folded within the range of $-\pi$ to $\pi$. Therefore, in order to require the accurate phases in the whole region of a brain, the folded phase values have to be corrected. In the embodiment, the phase values folded within the range of $-\pi$ to $\pi$ are corrected by using, for example, a region growing method.

Next, noise mask processing is performed on a region containing only noise components (noise region) of the phase image (Step S1303). According to the noise mask processing in the embodiment, at first, a mask image is created using the absolute value image. In the mask image, by using a predetermined threshold, the pixel value of a region having a smaller value than the threshold in the absolute value image is set at 0, and the pixel value of the other region is set at 1. Then, the phase image is multiplied by the created mask image. Here, the threshold may be required from the pixel value distribution of all pixels of the absolute value image, according to a method such as a discriminant analysis method.

There are various methods of the noise mask processing. For example, a method of defining the pixel value of an air region as 0 may be used to create a mask image for the noise mask processing. In this case, a boundary between the brain and air is detected and the air region is extracted based on the detected result. For the noise mask processing, another method like this may be used.

Then, processing for removing the boundary region between the brain and air from the phase image subjected to the noise mask processing is performed (Step S1304). The phase of the boundary region adjacent to the air is distinctive in the spatial variation compared to the phase of the other regions, which may cause an artifact in the calculated magnetic susceptibility image. Therefore, this boundary region has to be removed. In the boundary removal processing in the embodiment, a region is magnified from the air region in the phase image subjected to the noise mask processing according to the region growing method and when the phase value exceeds a predetermined threshold, the value is replaced with 0, thereby removing the boundary region. Here, there are various known methods of the removal processing of a boundary region. For example, a method of using the Gaussian function may be used to fit the phase variation in the boundary region and subtract the above from the original image. For the removal processing of the boundary region, another method like this may also be used.

The above four types of processing of the phase image processing as mentioned above are only one example and the processing is not restricted to the above example. Alternatively, some of the above four may be omitted. The order of the respective processing does not matter. In addition, the phase image processing may not be performed necessarily. When the phase image processing is not performed, noise and phase non-uniformity cannot be removed but an artifact may be generated on the magnetic susceptibility image calculated in Step S1203; however, a magnetic susceptibility image can be calculated for the small number of times and a short time of processing.

At last, from the phase image subjected to the phase image processing, a magnetic susceptibility image to display on the display 210 is calculated (Step S1203).

The embodiment includes the following processes of: at first, calculating a low frequency region magnetic susceptibility image $\chi_0$ that is a magnetic susceptibility image used for a low frequency region, from the phase image (Step S1401); calculating an edge information magnetic susceptibility image $\chi_g$ that is a magnetic susceptibility image including the edge information of a tissue on the magnetic susceptibility distribution, although the magnetic susceptibility value is not correct (Step S1402); calculating a high frequency region magnetic susceptibility image $\chi_c$ that is a magnetic susceptibility image used for a high frequency region (Step S1403); calculating an edge mask from the $\chi_g$ (Step S1404); smoothing the magnetic susceptibility value corresponding to a magic angle region from the edge mask and the low frequency region magnetic susceptibility image $\chi_0$ (Step S1405); and in the end, smoothing the magnetic susceptibility value corresponding to a high frequency region, using the high frequency region magnetic susceptibility image $\chi_c$ (Step S1406).

Here, a region dividing method of the k space on the magnetic susceptibility image calculation processing in the embodiment will be described before describing the concrete processes from Step S1401 to Step S1406.

Figure 9:
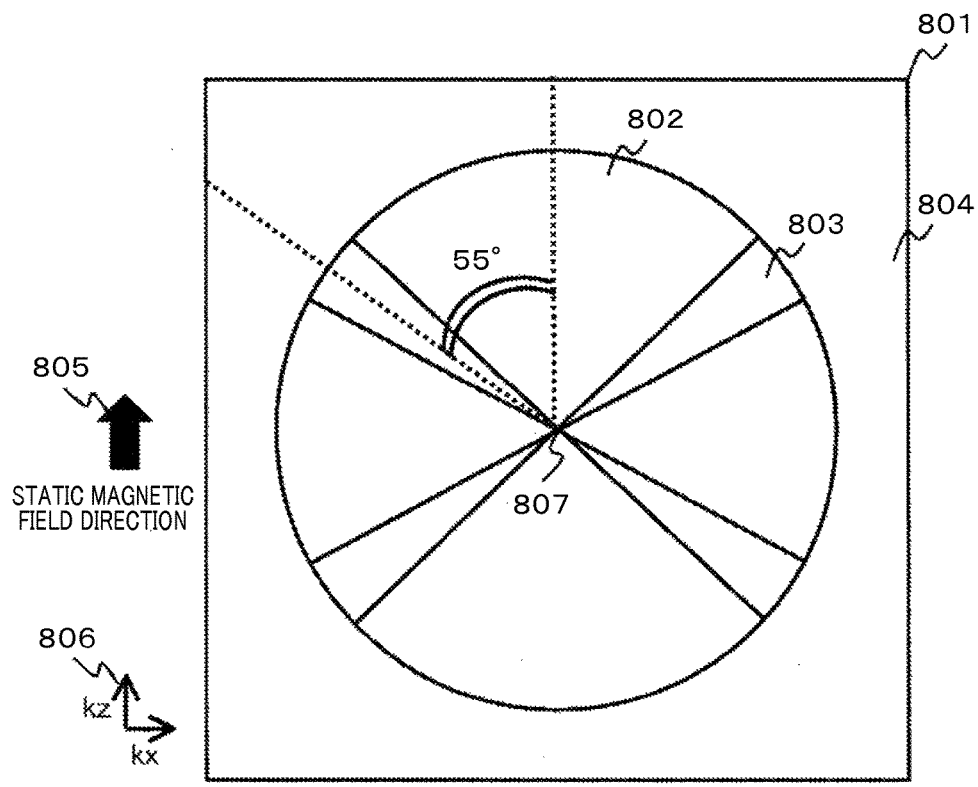
FIG. 9 is a schematic view of a k space region of a magnetic susceptibility image in the embodiment.
Figure 10:
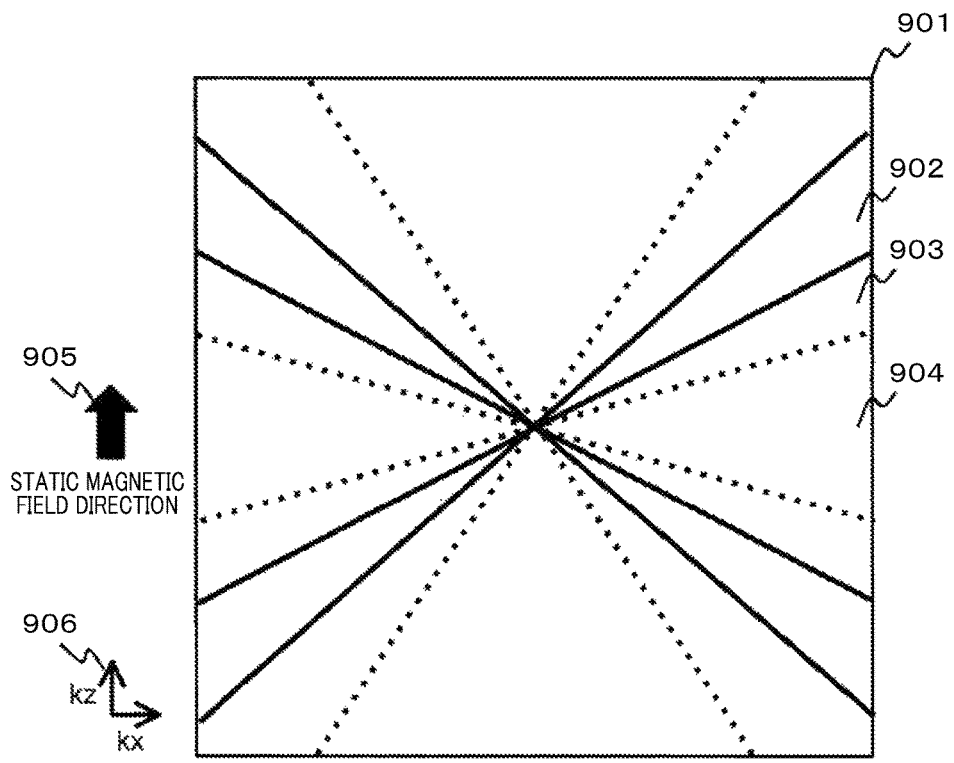
FIG. 10 is a schematic view of the k space region of the magnetic susceptibility image in the HEIDI method.

In the embodiment, the k space on the magnetic susceptibility image to be displayed on the display 210 is divided into three regions and different processing is respectively applied to the regions, using three different magnetic susceptibility images previously calculated. FIG. 9 illustrates a schematic view of the region division of the k space in the embodiment. As illustrated in FIG. 9, in the embodiment, the region is divided into a low frequency region 802 where the magnetic susceptibility information of tissue exists, a magic angle region 803 where the accuracy of the solution is much deteriorated, and a high frequency region 804 where contrast information of minute tissue exists although the magnetic susceptibility information is less than in the low frequency region.

In the embodiment, the magnetic susceptibility image $\chi_0$ which contains the information of a magnetic susceptibility value of a tissue is used for the low frequency region 802 although the background noise thereof is larger a desired value. In the embodiment, the magnetic susceptibility image $\chi_0$ used for the low frequency region is referred to as a low frequency region magnetic susceptibility image. For the magic angle region 803, the magnetic susceptibility image $\chi_g$ which contains the edge information of a tissue on the magnetic susceptibility distribution although the magnetic susceptibility value of the tissue is not correct, is previously calculated and the edge image calculated from the magnetic susceptibility image is used to do smoothing. In the embodiment, the magnetic susceptibility image $\chi_g$ used for calculation of the edge image is referred to as an edge information magnetic susceptibility image. For the high frequency region 804, the magnetic susceptibility image $\chi_c$ is used, which is calculated according to a regularization method using a regularization parameter of making CNR (contrast-to-noise ratio) maximum although the magnetic susceptibility value of a tissue is not correct. In the embodiment, the magnetic susceptibility image $\chi_g$ used for the high frequency region is referred to as a high frequency region magnetic susceptibility image.

The details of the above three dividing ways will be described later.

In the region division of a k space in the embodiment, smoothing is not performed in the low frequency region where the magnetic susceptibility information of a tissue exists, but performed in the high frequency region; therefore, the background noise can be reduced without reducing the magnetic susceptibility value of the tissue.

Further, in the magic angle region, the edge image is calculated from the edge information magnetic susceptibility image including correct edge information of the tissue on the magnetic susceptibility distribution and smoothing is performed by using this. The edge image calculated from the edge information magnetic susceptibility image $\chi_c$ agrees with the edge of a tissue on the magnetic susceptibility distribution and the edge does not change according to the static magnetic field direction. Therefore, estimation accuracy in the magnetic susceptibility of a tissue is more improved, compared to the case of smoothing by use of the edge image calculated from the absolute value image and the phase image.

The above mentioned three of the low frequency region magnetic susceptibility image $\chi_0$, the edge information magnetic susceptibility image $\chi_g$, the high frequency region magnetic susceptibility image $\chi_c$ in the embodiment are calculated according to the L1 norm regularization method. In the embodiment, by changing a regularization parameter in the L1 norm regularization method, magnetic susceptibility images of various properties are calculated. Here, a relation between the size of the regularization parameter according to the L1 norm regularization method and the property of the calculated magnetic susceptibility image will be described briefly. The L1 norm regularization method is to set the following evaluation function $e(\chi)$ using the relational expression of the formula (1) and to calculate the magnetic susceptibility image by minimizing the $e(\chi)$.

$$e(\chi)=\|W\cdot(C\chi-\delta)\|^2+\lambda\|\chi\|_1 \quad \text{(formula 5)}$$

Where, $\delta$ is a column vector of the phase image having a size of the total number of the pixels N, $\chi$ is a column vector of the magnetic susceptibility image, C is a matrix corresponding to the convolution operation on $\chi$, with a size of N×N, W is a column vector having a size of N and a coefficient vector for weighting error in each pixel. Further, · indicates multiplication of every vector element, $\|A\|$ indicates the norm of the vector A, $\gamma$ indicates an arbitrary constant, $\|A\|_1$ indicates the L1 norm of the vector A. The L1 norm $\|A\|_1$ of the vector A indicates the total sum of the absolute values of each element of the vector A.

In the formula (5), the first item is to reduce an error of the relational expression between the phase and the magnetic susceptibility, and the second item is to reduce the background noise. In the L1 norm regularization method, according to the size of the regularization parameter $\lambda$, the second item's contribution to the reduction of the background noise in the magnetic susceptibility image is controlled and the property of the magnetic susceptibility image is changed.

Basically, according to an increase in the regularization parameter $\gamma$, the background noise is reduced and simultaneously, the magnetic susceptibility of tissue is reduced. In the L1 norm regularization method, the reduction ratio of the background noise is larger than the reduction ratio of the magnetic susceptibility of a tissue in the range of some $\lambda$. Specifically, when the $\lambda$ is increased from 0, the estimation accuracy of the magnetic susceptibility becomes the maximum in some $\lambda_{-0}$. Further, when the $\lambda$ is increased from the $\lambda_0$, the background noise and the magnetic susceptibility of the tissue are reduced; however, until some value $\lambda_c$, the reduction ratio of the background noise is larger than the reduction ratio of the magnetic susceptibility of the tissue. Accordingly, the CNR defined by the ratio of the magnetic susceptibility difference between the tissue and the background noise has the maximum value in the $\lambda_c$. The magnetic susceptibility image calculated by $\lambda=\lambda_c$ is lower than the magnetic susceptibility image calculated by $\lambda=\lambda_0$ in the estimation accuracy of the magnetic susceptibility of the tissue, but smaller in the background noise and larger in the CNR. A relation between $\lambda_0$ and $\lambda_c$ is $\lambda_0<\lambda_c$. Similarly, when the $\lambda$ is increased from the $\lambda_0$, until some value $\lambda_g$, the reduction ratio of the background noise is larger than the reduction ratio of the magnetic susceptibility difference between outside and inside the tissue in the edge region of the target tissue. The accuracy of the edge image using the magnetic susceptibility image is in proportion to the ratio of the magnetic susceptibility difference between the inside and the outside of the tissue in the edge region and the background noise. Accordingly, the accuracy of the edge image using the magnetic susceptibility image calculated from the formula (5) becomes the maximum in the $\lambda_g$. The magnetic susceptibility image calculated by $\lambda=\lambda_g$ is lower than the magnetic susceptibility image calculated by $\lambda=\lambda_0$ in the estimation accuracy of the magnetic susceptibility of the tissue, but smaller in the background noise and larger in the accuracy of edge extraction of a target tissue. A relation between $\lambda_0$ and $\lambda_g$ is $\lambda_0<\lambda_g$. A regularization method of regularizing the L1 norm of the spatial gradient of the magnetic susceptibility image is similar to the above mentioned L1 norm regularization method.

Figure 8:
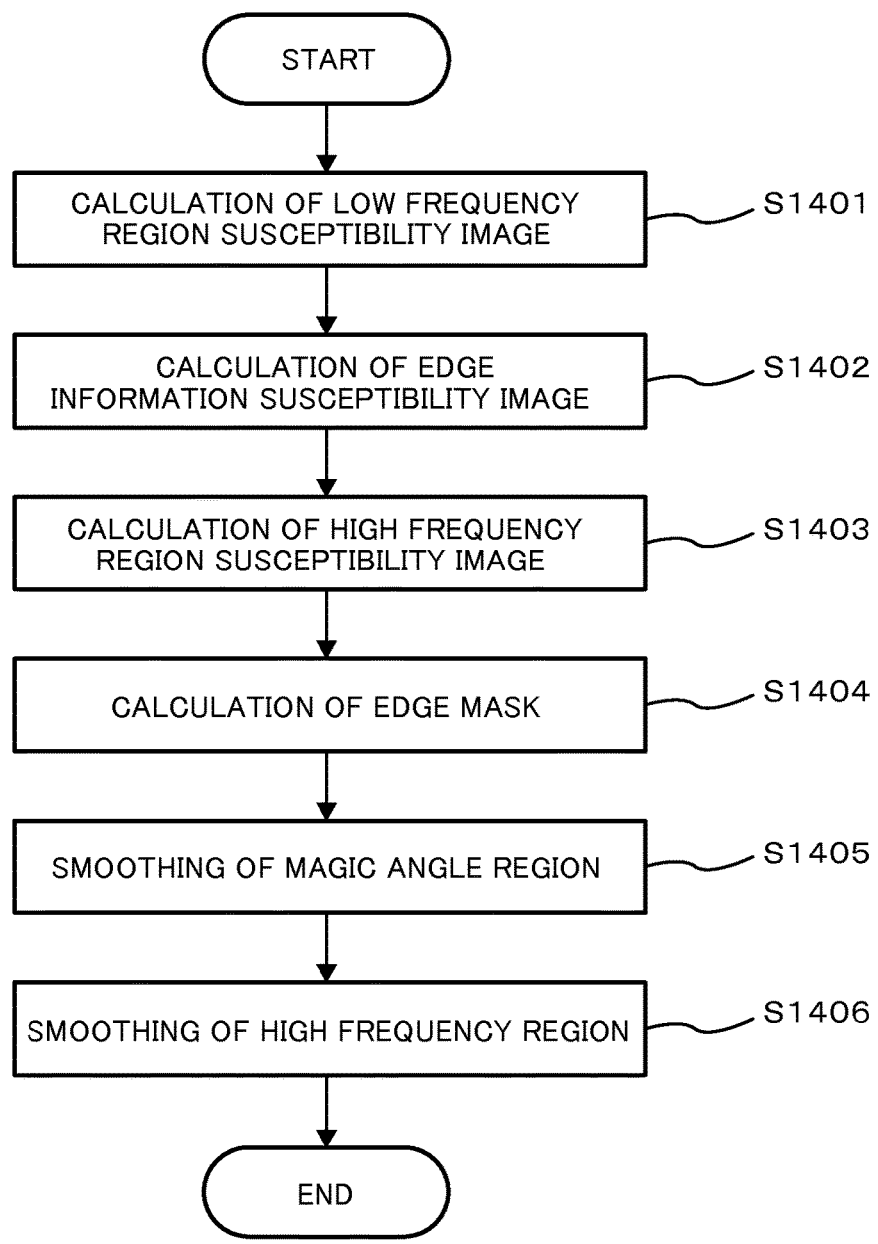
FIG. 8 is a flow chart of magnetic susceptibility image calculation processing in the embodiment.

Considering the region dividing method of the k space and the property of the regularization parameter in the L1 norm regularization method as mentioned above, the magnetic susceptibility image calculation procedure in the embodiment will be described according to the processing flow of FIG. 8.

At first, the low frequency region magnetic susceptibility image $\chi_o$ that is the magnetic susceptibility image used for a low frequency region is calculated (Step S1401).

The image $\chi_o$ in the embodiment is calculated according to the L1 norm regularization method of the formula (5), using the $\lambda$ having the most improved estimation accuracy of the magnetic susceptibility of the tissue. The estimation accuracy of the magnetic susceptibility of the tissue indicates a similarity of the magnetic susceptibility value of the tissue in the magnetic susceptibility distribution and the magnetic susceptibility value of the calculated magnetic susceptibility image of the tissue.

The estimation accuracy of the magnetic susceptibility of the tissue can be calculated, for example, through a computer simulation. In this case, for example, a magnetic susceptibility distribution is set for a model. The magnetic susceptibility distribution of the model uses, for example, a magnetic susceptibility image approximately calculated. Then, a phase image is calculated from the magnetic susceptibility distribution of the model, through the computer simulation, using the relational expression of the formula (1), and a magnetic susceptibility image is estimated from the calculated phase image, using the formula (5). Then, after calculating a relative error between the average magnetic susceptibility value of the target tissue on the magnetic susceptibility distribution of the model and the average magnetic susceptibility value of the target tissue on the magnetic susceptibility image estimated using the formula (5), the value of $\lambda$ when the relative error becomes the minimum is adopted. In the embodiment, the magnetic susceptibility image obtained with $\lambda=10^{-5}$ is defined as the low frequency region magnetic susceptibility image $\chi_o$. Further, in the embodiment, the coefficient vector W in the formula (5) is 1 in any case. In the embodiment, the value of $\chi_o$ which makes the evaluation function $e(\chi_o)$ minimum in the formula (5) is required by an iterative calculation according to the non-linear conjugate gradient method. As the condition of finishing the repetition of the non-linear conjugate gradient method, when the number of repetitions exceeds a predetermined number, the repetition is to be finished. Further, all the elements take the vector of 0 as the initial value of the iterative calculation.

Any value can be used for $\lambda$. The value of $\lambda$ may be always a constant value depending on the device and imaging method; alternatively, the above value may be automatically calculated according to the SN ratio (signal-to-noise ratio) of the absolute value image. Further, as the coefficient vector W, any vector such as the pixel value of the absolute value image can be used. Further, as the initial value of the iterative calculation, any vector can be used such as the magnetic susceptibility image obtained with a low resolution or the magnetic susceptibility image obtained by use of the Fourier transform. Further, the minimum value of the $\chi_o$ may be required by using a linear programming and the like. Further, as the repetition finishing condition, any condition can be used such as finishing when the $e(\chi_o)$ becomes smaller than the predetermined threshold. Further, any regularization method can be used such as the L2 norm regularization method or the method of regularizing the L1 norm of the spatial gradient of the magnetic susceptibility image. Alternatively, not the regularization method but another method can be used. For example, according to the relational expression on the k space in the formula (2), a magnetic susceptibility image on the k space may be required and it may be converted by the inverse Fourier transform, hence to require a magnetic susceptibility image on the actual space. Further, a phase image with a low resolution is calculated from the phase image and a low frequency region magnetic susceptibility image may be calculated from the low resolution phase image. Further, the magnetic susceptibility distribution of a model for use in calculating the estimation accuracy of the magnetic susceptibility of a tissue may be also optional. The estimation accuracy of the magnetic susceptibility can be calculated by any method.

Next, the edge information magnetic susceptibility image $\chi_g$ is calculated (Step S1401). The edge information magnetic susceptibility image $\chi_g$ in the embodiment is calculated by using the value of $\lambda$ that most improves the accuracy of the edge image. The accuracy of the edge image indicates how much correctly the edge image shows the edge information of a tissue in the magnetic susceptibility distribution. The accuracy of the edge image can be calculated, for example, using the computer simulation. In this case, for example, from the magnetic susceptibility image estimated using the formula (5), an edge mask to be calculated in the method of Step S1404 is calculated, the magnetic susceptibility value corresponding to the magic angle region is smoothed by using the calculated edge mask according to the method in Step S1405, and the $\lambda$ which makes the estimation accuracy of the magnetic susceptibility of the tissue a maximum in the smoothed magnetic susceptibility image is adopted. In the embodiment, the magnetic susceptibility image obtained with $\lambda=10^{-2}$ is defined as the edge information magnetic susceptibility image $\chi_g$. Further, the coefficient vector W in the formula (5), the method of minimizing the evaluation function $e(\chi_g)$, and the finishing condition of the minimizing calculation are the same as the method of Step S1401.

The value of $\lambda$, the coefficient vector W, the minimizing method of $e(\chi_g)$, and the finishing condition of the minimizing calculation in the formula (5) are optional, similarly to Step S1401. Further, the calculation method of the magnetic susceptibility image is also optional, similarly to Step S1401. Further, the calculation method of the accuracy of the edge image is also optional.

Then, the high frequency region magnetic susceptibility image $\chi_c$ is calculated (Step S1403). The image $\chi_c$ in the embodiment is calculated by using the value of $\lambda$ that most improves the CNR. In the embodiment, the CNR is calculated by dividing a difference between the average value of the magnetic susceptibility values of a target tissue and the average value of the magnetic susceptibility values of the white matter by the standard deviation of the magnetic susceptibility value of the white matter. The CNR can be defined by any definition. In the embodiment, the magnetic susceptibility image obtained with $\lambda=10^{-3}$ is defined as the high frequency region magnetic susceptibility image $\chi_c$. Further, the coefficient vector W, the method of minimizing the evaluation function $e(\chi_c)$, and the finishing condition of the minimizing calculation in the formula (5) are similar to the method of Step S1401.

The value of $\lambda$, the coefficient vector W, the minimizing method of $e(\chi_c)$, and the finishing condition of the minimizing calculation in the formula (5) are optional, similarly to Step S1401. Further, the calculation method of the magnetic susceptibility image is optional, similarly to Step S1401. Further, the magnetic susceptibility image obtained by multiplying the $\chi_c$ in the embodiment by a constant number may be defined as a new $\chi_c$.

Next, the edge mask calculation unit 534 calculates an edge image from the edge information magnetic susceptibility image $\chi_g$, and further calculates an edge mask from the edge image (Step S1404). The edge image in the embodiment is an image having a large spatially-changed region in the $\chi_g$ with a large pixel value and a small spatially-changed region with a small pixel value. In the embodiment, an edge image is calculated by calculating the gradient in three directions of x direction, y direction, and z direction of the $\chi_g$.

$$S_x = G_x \chi_g \quad \text{(formula 6)}$$

$$S_y = G_y \chi_g \quad \text{(formula 7)}$$

$$S_z = G_z \chi_g \quad \text{(formula 8)}$$

Where, $S_x$, $S_y$, and $S_z$ respectively indicate the edge image in the x direction, the y direction, and the z direction and $G_x$, $G_y$, and $G_z$ respectively indicate the operator for calculating the gradient of the image in the x direction, the y direction, and the z direction. In the embodiment, the gradient is defined by the value obtained by dividing a difference between the pixel values at both sides of the relevant pixel by the distance between the right and left pixels.

The gradient can be defined by any definition, such as the definition with the value obtained by dividing a difference between the pixel values of the adjacent pixels by the distance between the adjacent pixels. Further, the edge can be extracted according to an arbitrary method, such as filtering processing on the image with the Laplacian filter. Alternatively, a median filter may be used to smooth the edge information magnetic susceptibility image $\chi_g$, and then to calculate the edge image. Alternatively, the edge image may be smoothed by using the median filter.

Next, the edge mask calculation unit 534 calculates the edge mask of a tissue from the edge image. In the embodiment, the edge mask $W_x$ in the x direction of the pixel i is calculated by using the following formula.

$$W_x(i) = \begin{cases} 1 & (|S_x(i)| < a_w) \\ 0 & (|S_x(i)| > a_w) \end{cases} \quad \text{(formula 9)}$$

The edge mask of a tissue is an image having an edge region of the tissue with the pixel value 0 and the other region than the edge with the pixel value 1. The edge mask $W_x$ in the embodiment is a mask image having a large pixel value of 0 in the edge image $S_x$ and a small pixel value of 1 in the edge image $S_x$ with the threshold $a_w$ as a reference. Further, the threshold $a_w$ is defined as an edge mask threshold. The same calculation is performed also in the y direction and the z direction, hence to calculate $W_y$ and $W_z$. The value of the edge mask threshold $a_w$ in the embodiment is determined, for example, using a computer simulation, so that the estimation accuracy of the magnetic susceptibility of the tissue may be a maximum in the magnetic susceptibility image in which the magic angle region has been smoothed according to the method in Step S1405. Further, it is determined by using the ratio w of a region where the mask $W_x$, $W_y$, and $W_z$ is 1, of the whole brain region. In other words, when the number of the pixels in the whole brain region is defined as m and the number of the pixels which makes the $W_x$, $W_y$, and $W_z$ 1 is respectively defined as $w_x$, $w_y$, and $w_z$, the w is calculated as $w = (w_x + w_y + w_z)/3m$. In the embodiment, the edge mask threshold $a_w$ is determined to be w=0.35.

The edge mask calculation unit 534 may calculate an edge mask from a plurality of images such as the absolute value image and the previously obtained image and multiply $W_x$, $W_y$, and W, by the edge mask. Further, the edge mask threshold $a_w$ can be determined arbitrarily. The edge mask thresholds different in the x direction, the y direction, and the z direction may be used. Although each of $W_x$, $W_y$, and $W_z$ in the embodiment is constituted by only two values of 0 and 1, the boundary point may be constituted to gradually change between 1 and 0.

Then, the magic angle region smoothing unit 535 smooths the magnetic susceptibility value corresponding to a magic angle region, and calculates a magic smoothing magnetic susceptibility image $\chi_1$ (Step S1405). Magic angle region smoothing is to smooth the magnetic susceptibility value corresponding to a magic angle region and to reduce the background noise. In the embodiment, by performing the minimizing calculation of $g(\chi_1)$ in the following formula (10), magic angle region smoothing is performed from the low frequency region magnetic susceptibility image $\chi_0$ and the edge mask $W_x$, $W_y$, and $W_z$.

$$g(\chi_1) = \|M_k(FT(\chi_1) - FT(\chi_0))\|^2 + \lambda_1(\|W_x G_x \chi_1\|_1 + \|W_y G_y \chi_1\|_1 + \|W_z G_z \chi_1\|_1) \quad \text{(formula 10)}$$

Where, $\chi_1$ is a magic smoothing magnetic susceptibility image to be calculated, $M_k$ of the first item is a magic angle mask with the magic angle region defined as 0 and the other region defined as 1, and $\lambda_1$ is an arbitrary constant. The first item is to require the solution of the regions other than the magic angle on the k space of the magic smoothing magnetic susceptibility image $\chi_1$ to be the same as that of the low frequency region magnetic susceptibility image $\chi_0$. The second item is to approach the mutual pixel values of the adjacent pixels of the $\chi_1$ in the region where $W_x$, $W_y$, $W_z$ is 1. The second item is to smooth the region where $W_x$, $W_y$, $W_z$ is 1, in other words, the region other than the edge in the edge information magnetic susceptibility image $\chi_g$. With the size of the magic angle region in the embodiment defined by the magic angle threshold $a_{th}$, the region of $|1/3 - k_z^2/k^2| < a_{th}$ is defined as $M_k = 0$ and the other region is defined as $M_k = 1$. In the embodiment, the magic angle threshold $a_{th}$ and $\lambda_1$ are set at values having the maximum estimation accuracy of the magnetic susceptibility of a tissue in the $\chi_1$. Specifically, $a_{th} = 0.05$ and $\lambda_1 = 10^{-2}$ are used. Further, the solution of the formula (10) is calculated by the iterative calculation according to the non-linear conjugate gradient method and when the number of repetition exceeds a predetermined number, calculation is to be finished as a reference of the repetition finishing condition.

In the smoothing of the magic angle region in the embodiment, an edge image is calculated from the edge information magnetic susceptibility image $\chi_g$ to smooth the above region by using the edge image. The edge image calculated from the edge information magnetic susceptibility image $\chi_g$ agrees with the edge of a tissue on the magnetic susceptibility distribution and the edge does not change depending on the direction of the static magnetic field. Therefore, compared to the case of smoothing by use of the edge image calculated from the absolute value image and the phase image, the estimation accuracy of the magnetic susceptibility of a tissue is improved. Further, similarly to the case of smoothing by use of the edge image calculated from the absolute value image and the phase image, the background noise is reduced by the effect of the smoothing.

In the magic angle mask $M_k$, only the magic angle region in a low frequency region may be defined as 0. Further, in the embodiment, although the $M_k$ consists of only two values of 0 and 1, the interval between 0 and 1 may be gradually changed in the boundary point of $|1/3 - \lambda_z^2/k^2| = a_{th}$. Any value can be used for the magic angle threshold $a_{th}$ and $\lambda_1$. Further, the solution of the formula (10) can be calculated according to an arbitrary method such as linear programming. As the repetition finishing condition, any condition can be used such as finishing when the $g(\chi_1)$ is smaller than the predetermined threshold. Further, any formulation can be used for the smoothing in the magic angle region. For example, under the condition satisfying the following formula (11), $h(\chi_1)$ represented by the formula (12) may be minimized.

$$M_k FT(\chi_1) = M_k FT(\chi_0) \quad \text{(formula 11)}$$

$$h(\chi_1) = \|W_x G_x \chi_1\|_1 + \|W_y G_y \chi_1\|_1 + \|W_z G_z \chi_1\|_1 \quad \text{(formula 12)}$$

In the end, the high frequency region smoothing unit 536 smooths a high frequency region and calculates a high frequency smoothing magnetic susceptibility image $\chi_L$ (Step S1406). Smoothing of a high frequency region is the processing to smooth the magnetic susceptibility value corresponding to the high frequency region on the k space of a magnetic susceptibility image and reduce the background noise of the magnetic susceptibility image. In the high frequency region smoothing processing of the embodiment, a high frequency region is replaced with a high frequency region magnetic susceptibility image $\chi_c$ calculated by the high frequency region magnetic susceptibility image calculation unit 533. In other words, the k space signal $X_L$ of the high frequency smoothing magnetic susceptibility image is obtained according to the formula (13).

$$X_L(k) = \begin{cases} X_1(k) & (|k| < k_{th}) \\ X_C(k) & (|k| \geq k_{th}) \end{cases} \quad \text{(formula 13)}$$

Where, k is a positional vector on the k space, $\chi_1$ is the k space signal of the magic smoothing magnetic susceptibility image $\chi_1$, and $X_c$ is the k space signal of the high frequency region magnetic susceptibility image $\chi_c$. In the embodiment, the boundary between the high frequency region and the low frequency region is defined by the distance $|k| = \sqrt{(k_x^2 + k_y^2 + k_z^2)}$ from the origin center of the k space. Using some threshold $k_{th}$, the region of $|k| < k_{th}$ is defined as the low frequency region and the region of $|k| \geq k_{th}$ is defined as the high frequency region. Further, this $k_{th}$ is referred to as a division point. In the embodiment, the division point $k_{th}$ adopts the value when the background noise is most reduced without reducing the magnetic susceptibility estimation accuracy of a tissue. Concretely, $k_{th} = 0.4$. The high frequency smoothing magnetic susceptibility image $\chi_L$ can be calculated by performing the inverse Fourier transform on $X_L$.

Information about the magnetic susceptibility of a tissue mainly exists in the low frequency components. Therefore, by replacing the high frequency region with the high frequency region magnetic susceptibility image $\chi_c$ having a small background noise and a large CNR, the background noise can be reduced while keeping the magnetic susceptibility of tissue and the contrast as much as possible. The high frequency region magnetic susceptibility image $\chi_c$ in the embodiment is calculated according to the L1 regularization method for smoothing with contrast of minute structure enhanced. Therefore, even when the high frequency region magnetic susceptibility image $\chi_c$ is used for the high frequency region, the contrast information of the minute structure existing in the high frequency region is not lost according to the effect of the smoothing.

As the method of smoothing the high frequency region, not only the method of replacing with the image having a large CNR but any method can be used. For example, an arbitrary regularization method can be used to do the smoothing and the filter processing such as a median filter can be performed to do the smoothing. Any value can be used for the division point $k_{th}$. For example, the value when the background noise is most reduced without reducing the magnetic susceptibility value of the tissue can be used. Further, in the embodiment, the images $X_1$ and $X_c$ are mixed to change step by step in the division point of the high frequency region and the low frequency region; however, the $X_1$ and $X_c$ may be mixed in away that the ratio of $X_1$ and $X_c$ gradually changes. In the embodiment, although the high frequency region and the low frequency region are divided in two stages, they may be divided in any number of stages such as three stages and the different processing may be respectively applied.

When the background noise can be reduced to a desired degree according to the processing up to Step S1405, Step S1406 may be omitted. In this case, Step S1403 may be omitted. Alternatively, the order of Step S1405 and Step S1406 may be reversed.

In the embodiment, the high frequency smoothing magnetic susceptibility image $\chi_L$ is calculated by using the edge image capable of correctly extracting the edge of a tissue without a contrast change depending on a magnetic field direction; therefore, it is possible to estimate a magnetic susceptibility of a tissue with high accuracy. Further, by smoothing the high frequency region, it is possible to reduce the background noise without reducing the magnetic susceptibility value of the tissue. According to this, the magnetic susceptibility of the tissue can be calculated with less background noise and with high accuracy.

Alternatively, according to an arbitrary combination of processing Step S1401 to S1406 in the magnetic susceptibility image calculation processing in the embodiment, various magnetic susceptibility images can be calculated. For example, a low frequency region magnetic susceptibility image $\chi_0$ is calculated through the low frequency region magnetic susceptibility image calculation processing (Step S1401), a high frequency region magnetic susceptibility image $\chi_c$ is calculated through the high frequency region magnetic susceptibility image calculation processing (Step S1403), and through the high frequency region smoothing processing (Step S1406), a magnetic susceptibility image $\chi_L$ with these two images mixed may be calculated. In this case, the magic angle region smoothing processing is not performed; therefore, compared to the high frequency smoothing magnetic susceptibility image $\chi_L$ calculated in the embodiment, the estimation accuracy of the magnetic susceptibility of the tissue is reduced and the background noise is increased; however, the magnetic susceptibility image $\chi_L$ can be calculated with a less number of processing steps.

Alternatively, the edge information magnetic susceptibility image $\chi_g$ is calculated through the edge information magnetic susceptibility image calculation processing (Step S1402), the edge masks $W_x$, $W_y$, and W, are calculated from the edge information magnetic susceptibility image $\chi_g$-through the edge mask calculation processing (Step S1404), and the magnetic susceptibility image $\chi_{L2}$ may be calculated, for example, by performing the minimizing calculation on $g(\chi_{L2})$ in the following formula (14).

$$g(\chi_{L2}) = \|W \cdot (C\chi_{L2} - \delta)\|^2 + \lambda_1 (\|W_x G_x \chi_{L2}\|_1 + \|W_y G_y \chi_{L2}\|_1 + \|W_z G_z \chi_{L2}\|_1) \quad \text{(formula 14)}$$

Here, the first item of the formula (14) is the same as the first item of the formula (5) and the second item thereof is the same as the second item of the formula (10). In this case, the low frequency region other than the magic angle region is also smoothed, and therefore, the magnetic susceptibility value of the tissue is reduced. Therefore, compared to the high frequency smoothing magnetic susceptibility image $\chi_L$ calculated in the embodiment, the estimation accuracy of the magnetic susceptibility of the tissue is reduced; however, the magnetic susceptibility image $\chi_{L2}$ can be calculated with a less number of processing steps.

Alternatively, the magic smoothing magnetic susceptibility image $\chi_1$ and the high frequency smoothing magnetic susceptibility image $\chi_L$ calculated in the embodiment may be defined as the edge information magnetic susceptibility image $\chi_g'$, and the magnetic susceptibility image calculation processing in the embodiment may be performed again, to calculate a new magic smoothing magnetic susceptibility image $\chi_1'$ and a new high frequency smoothing magnetic susceptibility image $\chi_L'$. The edge information magnetic susceptibility image $\chi_g'$ has a better accuracy in the edge image than the edge information magnetic susceptibility image $\chi_g$ in the embodiment. Therefore, the high frequency smoothing magnetic susceptibility image $\chi_L'$ is subjected to a larger number of the processing steps necessary for calculation than the high frequency smoothing magnetic susceptibility image $\chi_L$ in the embodiment but the estimation accuracy of the magnetic susceptibility of the tissue in the image $\chi_L'$ is better than that in the $\chi_L$. Alternatively, the magic smoothing magnetic susceptibility image $\chi_1'$ and the high frequency smoothing magnetic susceptibility image $\chi_L'$ calculated according to the above mentioned method may be defined as a new edge information magnetic susceptibility image $\chi_g''$, and the magnetic susceptibility image calculation processing of the embodiment may be performed again to calculate a new magic smoothing magnetic susceptibility image $\chi_L''$ and a new high frequency smoothing magnetic susceptibility image $\chi_L''$. Further, a series of processing may be performed for a plurality of times.

Although in the embodiment, the horizontal magnetic field type MRI device has been described, the same processing can be applied to a vertical magnetic field type MRI device and the like and the same effect can be obtained. Further, the same processing can be applied to any imaging cross section such as horizontal cross section, coronal cross section, sagittal cross section, and oblique cross section and the same effect can be obtained in any case.

Further, a complex image is not converted into an absolute value image and a phase image but the magnetic susceptibility image calculation processing may be directly performed on the complex image.

Further, a calculation method of an edge image and a smoothing method of a high frequency region in the embodiment can be applied to something other than the calculation of a magnetic susceptibility image. For example, the above can be used for calculation of distribution of T1 and T2 quantitative values and calculation of conductivity distribution.

In the embodiment, although the respective functions of the image reconstruction unit, the image conversion unit, and the display processing unit have been described by taking the case of realizing the above functions in a computer included in the MRI device as an example, they are not restricted to this. At least one of these units may be constructed, for example, on an information processor, independent from the MRI device, capable of transmitting and receiving data from and to the computer 209 of the MRI device.

In the above mentioned embodiment, as a basic concept, the k spatial region is divided into at least three regions of a low frequency region, a magic angle region, and a high frequency region and the different processing is respectively applied to the regions; however, it is not restricted to this but it may be minutely divided into more regions.

REFERENCE SIGNS LIST

101: Vertical magnetic field MRI device, 102: horizontal magnetic field MRI device, 103: MRI device, 201: magnet, 202: gradient magnetic field coil, 203: subject, 204: sequencer, 205: gradient magnetic field power supply, 206: high frequency magnetic field generator, 207: probe, 208: receiver, 209: computer, 210: display, 211: storage, 300: measurement unit, 400: image reconstruction unit, 500: image conversion unit, 510: complex image conversion unit, 520: phase image processing unit, 530: magnetic susceptibility image calculation unit, 531: low frequency region magnetic susceptibility image calculation unit, 532: edge information magnetic susceptibility image calculation unit, 533: high frequency region magnetic susceptibility image calculation unit, 534: edge mask calculation unit, 535: magic angle region smoothing unit, 536: high frequency region smoothing unit, 600: display processing unit, 701: slice gradient magnetic field pulse, 702: RF pulse, 703: slice encoding gradient magnetic field pulse, 704: phase encoding gradient magnetic field pulse, 705: readout gradient magnetic field pulse, 706: readout gradient magnetic field pulse, 707: echo, 708: slice encoding gradient magnetic field pulse, 709: phase encoding gradient magnetic field pulse, 801: k space, 802: low frequency region, 803: magic angle region, 804: high frequency region, 805: static magnetic field direction, 806: k space coordinate, 807: origin center, 901: k space 902: magic angle region, 903: peripheral region of magic angle, 904: region excluding magic angle and its periphery, 905: static magnetic field direction, 906: k space coordinate

The invention claimed is:
1. A magnetic resonance imaging device comprising:
a static magnetic field generator to apply a static magnetic field to a subject;
a gradient magnetic field generator to apply a gradient magnetic field to the subject;
a high frequency magnetic field pulse generator to irradiate the subject with a high frequency magnetic field pulse;
a receiver to receive a nuclear magnetic resonance signal from the subject; and
a computer programmed to control the gradient magnetic field and the high frequency magnetic field pulse,
wherein the computer is further programmed to:
detect the nuclear magnetic resonance signal generated from the subject as a complex signal by applying the high frequency magnetic field pulse and the gradient magnetic field to the subject placed in the static magnetic field,
reconstruct a complex image, in which each pixel value of the complex image is a complex number, from the complex signal,
convert the complex image into a magnetic susceptibility image by creating an absolute value image and a phase image from the complex image,
create a processed magnetic susceptibility image from the phase image including:
a step for calculating a low frequency region magnetic susceptibility image for a low frequency region of a k-space of the phase image;

a step for calculating an edge information magnetic susceptibility image indicating an edge of a tissue in a magnetic susceptibility distribution, a step for calculating a high frequency region susceptibility image for a high frequency region of the k-space;

a step for calculating an edge mask of a tissue from the edge information magnetic susceptibility image;

a step for smoothing magnetic susceptibility values in a magic angle region of the k-space using the edge mask and the low frequency region magnetic susceptibility image; and a step for replacing magnetic susceptibility values in the high frequency region of the k-space using the high frequency region susceptibility image, and display the low frequency region, the smoothed magic angle region and the replaced high frequency region as the processed magnetic susceptibility image on a display.

2. The device according to claim 1, wherein the phase image is processed according to a regularization method using a regularization parameter which improves a contrast-to-noise ratio of the processed magnetic susceptibility image.

3. The device according to claim 1, wherein the low frequency region magnetic susceptibility image is estimated by a regularization method using a first regularization parameter which improves the estimation accuracy of the magnetic susceptibility.

4. The device according to claim 3, wherein the first regularization parameter used for calculation of the low frequency region magnetic susceptibility image is smaller than a second regularization parameter used for calculation of the edge information magnetic susceptibility image.

5. The device according to claim 1, wherein a size of the magic angle region is set to maximize an estimation accuracy of the magnetic susceptibility of the tissue.

6. The device according to claim 1, where the high frequency region magnetic susceptibility image is estimated by an L1 norm regularization method.

7. The device according to claim 6, wherein a first regularization parameter for the high frequency region improves a contrast-to-noise ratio of the high frequency region magnetic susceptibility image.

8. The device according to claim 7, wherein the first regularization parameter used for calculating the high frequency region magnetic susceptibility image is larger than a second regularization parameter used for calculating the low frequency region magnetic susceptibility image.

9. The device according to claim 1, wherein a division point between the high frequency region and the low frequency region is set to reduce a background noise without reducing an estimation accuracy of the magnetic susceptibility.

* * * * *